(12) United States Patent
Drzyzga et al.

(10) Patent No.: US 7,918,792 B2
(45) Date of Patent: Apr. 5, 2011

(54) SURGICAL RETRACTOR FOR USE WITH MINIMALLY INVASIVE SPINAL STABILIZATION SYSTEMS AND METHODS OF MINIMALLY INVASIVE SURGERY

(75) Inventors: Anne Drzyzga, Taunton, MA (US); William Frasier, New Bedford, MA (US); Michael Zajack, Marshfield, MA (US); Michael DeFusco, North Attleboro, MA (US); Connie Marchek, Foxboro, MA (US); Nicholas Pavento, Walpole, MA (US); Ginger Boyer, North Attleboro, MA (US); Sara Dziedzic, Braintree, MA (US)

(73) Assignee: DePuy Spine, Inc., Raynham, MA (US)

( * ) Notice: Subject to any disclaimer, the term of this patent is extended or adjusted under 35 U.S.C. 154(b) by 618 days.

(21) Appl. No.: 11/325,269

(22) Filed: Jan. 4, 2006

(65) Prior Publication Data
US 2008/0021285 A1    Jan. 24, 2008

(51) Int. Cl.
*A61B 1/32* (2006.01)
*A61B 17/88* (2006.01)

(52) U.S. Cl. ........ 600/215; 600/219; 600/227; 606/279; 606/86 A

(58) Field of Classification Search .................. 600/201, 600/219, 215, 277
See application file for complete search history.

(56) References Cited

U.S. PATENT DOCUMENTS

| | | |
|---|---|---|
| 447,761 A | 3/1891 | Clough |
| 475,975 A | 5/1892 | Clough |
| 563,236 A | 6/1896 | Penhall |
| 2,053,868 A | 12/1935 | Grosso |
| 2,320,709 A | 6/1943 | Arnesen |
| 3,246,646 A | 4/1966 | Murphy, Jr. |
| 3,486,505 A | 12/1969 | Morrison |
| 3,522,799 A | 8/1970 | Gauthier |
| 3,771,518 A | 11/1973 | Greissing |
| 3,848,601 A | 11/1974 | Ma |
| 3,965,890 A | 6/1976 | Gauthier |
| 4,010,741 A | 3/1977 | Gauthier |
| 4,130,113 A | 12/1978 | Graham |
| 4,156,424 A | 5/1979 | Burgin |
| 4,254,763 A | 3/1981 | McCready |
| 4,263,899 A | 4/1981 | Burgin |
| 4,274,398 A | 6/1981 | Scott |

(Continued)

FOREIGN PATENT DOCUMENTS

EP    1192905    4/2002

(Continued)

OTHER PUBLICATIONS

Mayer, H.M. MD., "A New Microsurgical Technique for Minimally Invasive Anterior Lumbar Interbody Fusion", Spine; vol. 22(6); 1997; pp. 691-700.

*Primary Examiner* — Thomas C Barrett
*Assistant Examiner* — Nicholas Woodall

(57) ABSTRACT

A surgical retractor for use with a spinal stabilization system including a plurality of bone anchors and a plurality of anchor extensions. The surgical retractor includes a frame positionable between a first anchor extension connected to a first bone anchor implanted in a first vertebra and a second anchor extension connected to a second bone anchor implanted in a second vertebra and a first retractor blade connectable to the frame for retracting tissue between the first anchor extension and the second anchor extension.

10 Claims, 10 Drawing Sheets

U.S. PATENT DOCUMENTS

| | | |
|---|---|---|
| 4,421,107 A | 12/1983 | Estes |
| 4,434,791 A | 3/1984 | Darnell |
| 4,545,374 A | 10/1985 | Jacobson |
| 4,562,832 A | 1/1986 | Wilder |
| 4,573,448 A | 3/1986 | Kambin |
| 4,686,966 A | 8/1987 | Tsai |
| 4,765,311 A | 8/1988 | Kulik |
| 4,817,587 A | 4/1989 | Janese |
| 4,862,891 A | 9/1989 | Smith |
| 4,872,451 A | 10/1989 | Moore |
| 4,907,132 A | 3/1990 | Parker |
| 4,934,352 A | 6/1990 | Sullivan, Jr. |
| 5,000,163 A | 3/1991 | Ray |
| 5,052,372 A | 10/1991 | Michelson |
| 5,052,373 A | 10/1991 | Michelson |
| 5,125,396 A | 6/1992 | Ray |
| 5,135,525 A | 8/1992 | Biscoping |
| 5,158,543 A | 10/1992 | Lazarus |
| 5,171,279 A | 12/1992 | Mathews |
| 5,231,973 A | 8/1993 | Dickie |
| 5,231,974 A | 8/1993 | Giglio |
| 5,242,443 A | 9/1993 | Kambin |
| 5,279,567 A | 1/1994 | Ciaglia |
| 5,284,129 A | 2/1994 | Agbodoe |
| 5,292,309 A | 3/1994 | Van Tassel |
| 5,304,183 A | 4/1994 | Gourlay |
| 5,312,360 A | 5/1994 | Behl |
| 5,342,384 A | 8/1994 | Sugarbaker |
| 5,375,481 A | 12/1994 | Cabrera |
| 5,400,774 A | 3/1995 | Villalta |
| 5,415,666 A | 5/1995 | Gourlay |
| 5,429,121 A | 7/1995 | Gadelius |
| 5,439,464 A | 8/1995 | Shapiro |
| 5,472,426 A | 12/1995 | Bonati |
| 5,493,464 A | 2/1996 | Koshikawa |
| 5,503,617 A | 4/1996 | Jako |
| 5,509,893 A | 4/1996 | Pracas |
| 5,520,610 A | 5/1996 | Giglio |
| 5,554,101 A | 9/1996 | Matula |
| 5,569,248 A | 10/1996 | Mathews |
| 5,667,481 A | 9/1997 | Villalta |
| 5,681,265 A | 10/1997 | Maeda |
| 5,702,177 A | 12/1997 | Lin |
| 5,728,046 A * | 3/1998 | Mayer et al. .................. 600/210 |
| 5,728,097 A | 3/1998 | Mathews |
| 5,746,720 A | 5/1998 | Stouder |
| 5,755,660 A | 5/1998 | Tyagi |
| 5,762,629 A | 6/1998 | Kambin |
| 5,769,782 A | 6/1998 | Phan |
| 5,779,629 A | 7/1998 | Hohlen |
| 5,792,044 A | 8/1998 | Foley |
| 5,810,721 A | 9/1998 | Mueller |
| 5,813,978 A | 9/1998 | Jako |
| 5,816,257 A | 10/1998 | Chin |
| 5,875,782 A | 3/1999 | Ferrari |
| 5,879,291 A | 3/1999 | Kolata |
| 5,882,344 A | 3/1999 | Stouder |
| 5,891,147 A | 4/1999 | Moskovitz |
| 5,893,831 A | 4/1999 | Koros |
| 5,897,490 A | 4/1999 | Fox |
| 5,899,901 A | 5/1999 | Middleton |
| 5,902,231 A | 5/1999 | Foley |
| 5,902,233 A | 5/1999 | Farley |
| 5,902,315 A | 5/1999 | Dubois |
| 5,928,139 A * | 7/1999 | Koros et al. .................. 600/205 |
| 5,931,777 A | 8/1999 | Sava |
| 5,944,658 A * | 8/1999 | Koros et al. .................. 600/232 |
| 5,947,896 A | 9/1999 | Sherts |
| 5,951,467 A | 9/1999 | Picha |
| 5,954,635 A | 9/1999 | Foley |
| 5,967,970 A | 10/1999 | Cowan |
| 5,967,972 A | 10/1999 | Santilli |
| 5,967,973 A | 10/1999 | Sherts |
| 5,968,098 A | 10/1999 | Winslow |
| 5,976,146 A | 11/1999 | Ogawa |
| 5,981,147 A | 11/1999 | Hallock |
| 5,984,867 A | 11/1999 | Deckman |
| 6,030,340 A | 2/2000 | Maffei |
| 6,033,406 A | 3/2000 | Mathews |
| 6,042,542 A | 3/2000 | Koros |
| 6,048,309 A | 4/2000 | Flom |
| 6,063,088 A | 5/2000 | Winslow |
| 6,074,343 A | 6/2000 | Nathanson |
| 6,083,154 A | 7/2000 | Liu |
| 6,090,043 A | 7/2000 | Austin |
| 6,090,113 A | 7/2000 | Le Couedic |
| 6,120,434 A | 9/2000 | Kimura |
| 6,139,493 A * | 10/2000 | Koros et al. .................. 600/215 |
| 6,142,935 A | 11/2000 | Flom |
| 6,152,871 A | 11/2000 | Foley |
| 6,159,179 A | 12/2000 | Simonson |
| 6,162,170 A | 12/2000 | Foley |
| 6,176,823 B1 | 1/2001 | Foley |
| 6,187,000 B1 | 2/2001 | Davison |
| 6,197,002 B1 | 3/2001 | Peterson |
| 6,200,263 B1 | 3/2001 | Person |
| 6,206,822 B1 | 3/2001 | Foley |
| 6,206,862 B1 | 3/2001 | Giamanco |
| 6,217,509 B1 | 4/2001 | Foley |
| 6,224,545 B1 | 5/2001 | Cocchia |
| 6,224,608 B1 | 5/2001 | Ciccolella |
| 6,241,659 B1 | 6/2001 | Bookwalter |
| 6,261,295 B1 | 7/2001 | Nicholson |
| 6,264,650 B1 | 7/2001 | Hovda |
| 6,267,763 B1 | 7/2001 | Castro |
| 6,277,094 B1 | 8/2001 | Schendel |
| 6,293,950 B1 | 9/2001 | Lynch |
| 6,306,170 B2 | 10/2001 | Ray |
| 6,322,500 B1 | 11/2001 | Sikora |
| 6,331,157 B2 | 12/2001 | Hancock |
| 6,342,036 B1 | 1/2002 | Cooper |
| 6,371,959 B1 | 4/2002 | Trice |
| 6,371,968 B1 | 4/2002 | Kogasaka |
| 6,395,007 B1 | 5/2002 | Bhatnagar |
| 6,416,465 B2 | 7/2002 | Brau |
| 6,416,468 B2 | 7/2002 | Deckman |
| 6,427,034 B1 | 7/2002 | Meis |
| 6,431,025 B1 | 8/2002 | Koros |
| 6,461,330 B1 | 10/2002 | Miyagi |
| 6,464,634 B1 | 10/2002 | Fraser |
| 6,468,207 B1 | 10/2002 | Fowler |
| 6,520,907 B1 | 2/2003 | Foley |
| 6,527,466 B1 | 3/2003 | Blier |
| 6,530,880 B2 | 3/2003 | Pagliuca |
| 6,530,883 B2 | 3/2003 | Bookwalter |
| 6,530,926 B1 | 3/2003 | Davison |
| 6,537,212 B2 | 3/2003 | Sherts |
| 6,592,582 B2 | 7/2003 | Hess |
| 6,599,292 B1 * | 7/2003 | Ray .......................... 606/90 |
| 6,616,605 B2 | 9/2003 | Wright |
| 6,639,965 B1 | 10/2003 | Hsieh |
| 6,656,176 B2 | 12/2003 | Hess |
| 6,659,945 B2 | 12/2003 | Ball |
| 6,679,833 B2 | 1/2004 | Smith |
| 6,689,054 B2 | 2/2004 | Furnish |
| 6,692,434 B2 | 2/2004 | Ritland |
| 6,712,825 B2 | 3/2004 | Aebi |
| 6,716,218 B2 | 4/2004 | Holmes |
| 6,723,043 B2 | 4/2004 | Kleeman |
| 6,729,205 B2 | 5/2004 | Phillips |
| 6,733,445 B2 | 5/2004 | Sherts |
| 6,740,102 B2 | 5/2004 | Hess |
| 6,755,839 B2 | 6/2004 | Van Hoeck |
| 6,764,444 B2 | 7/2004 | Wu |
| 6,793,656 B1 | 9/2004 | Mathews |
| 6,814,700 B1 | 11/2004 | Mueller |
| 6,869,398 B2 | 3/2005 | Obenchain |
| 6,593,394 B1 | 5/2005 | Douglas |
| 6,893,394 B2 | 5/2005 | Douglas |
| 6,896,680 B2 | 5/2005 | Michelson |
| 6,939,297 B2 | 9/2005 | Gannoe |
| 6,945,933 B2 | 9/2005 | Branch |
| 6,951,538 B2 | 10/2005 | Ritland |
| 6,982,740 B2 | 1/2006 | Adair |
| 7,008,432 B2 | 3/2006 | Schlapfer |
| 7,052,497 B2 | 5/2006 | Sherman |
| 7,074,226 B2 | 7/2006 | Roehm |

| | | |
|---|---|---|
| 7,081,118 B2 | 7/2006 | Weber |
| 7,087,055 B2 | 8/2006 | Lim |
| 7,097,647 B2 | 8/2006 | Segler |
| 7,150,714 B2 | 12/2006 | Myles |
| 7,156,085 B2 | 1/2007 | Thalgott |
| 7,179,225 B2 | 2/2007 | Shluzas |
| 7,179,261 B2 | 2/2007 | Sicvol |
| 7,198,598 B2 | 4/2007 | Smith |
| 7,207,949 B2 | 4/2007 | Miles |
| 7,223,233 B2 | 5/2007 | Branch |
| 7,250,052 B2 | 7/2007 | Landry |
| 7,261,688 B2 | 8/2007 | Smith |
| 7,264,589 B2 | 9/2007 | Sharratt |
| 7,491,168 B2 | 2/2009 | Raymond |
| 7,556,601 B2 | 7/2009 | Branch |
| 2001/0029377 A1 | 10/2001 | Aebi |
| 2002/0002324 A1 | 1/2002 | McManus |
| 2002/0058948 A1 | 5/2002 | Arlettaz |
| 2003/0149341 A1* | 8/2003 | Clifton ............ 600/210 |
| 2003/0220650 A1 | 11/2003 | Major |
| 2004/0034351 A1* | 2/2004 | Sherman et al. ........ 606/61 |
| 2004/0087833 A1 | 5/2004 | Bauer |
| 2004/0138662 A1* | 7/2004 | Landry et al. .......... 606/61 |
| 2004/0230191 A1* | 11/2004 | Frey et al. ............ 606/57 |
| 2004/0242969 A1 | 12/2004 | Sherts |
| 2005/0243592 A1 | 2/2005 | Boyd |
| 2005/0131422 A1 | 6/2005 | Anderson |
| 2005/0137461 A1 | 6/2005 | Marchek |
| 2005/0159650 A1 | 7/2005 | Raymond |
| 2005/0159651 A1 | 7/2005 | Raymond |
| 2005/0171551 A1 | 8/2005 | Sukovich |
| 2005/0215866 A1 | 9/2005 | Kim |
| 2006/0074278 A1 | 4/2006 | Petit |
| 2006/0084844 A1* | 4/2006 | Nehls ............ 600/227 |
| 2006/0195017 A1 | 8/2006 | Shluzas |
| 2006/0207612 A1 | 9/2006 | Jackson |
| 2006/0224044 A1 | 10/2006 | Marchek |
| 2006/0247651 A1 | 11/2006 | Roehm |
| 2007/0038033 A1 | 2/2007 | Jones |
| 2007/0060795 A1 | 3/2007 | Vayser |
| 2007/0106123 A1 | 5/2007 | Gorek |
| 2007/0156023 A1 | 7/2007 | Frasier |
| 2007/0156024 A1 | 7/2007 | Frasier |
| 2007/0156025 A1 | 7/2007 | Marchek |
| 2007/0156026 A1 | 7/2007 | Frasier |
| 2007/0208228 A1 | 9/2007 | Pavento |
| 2008/0021285 A1 | 1/2008 | Drzyzga |
| 2009/0018399 A1 | 1/2009 | Martinelli |

FOREIGN PATENT DOCUMENTS

| | | |
|---|---|---|
| FR | 2807313 | 10/2001 |
| WO | 0180725 | 11/2001 |

* cited by examiner

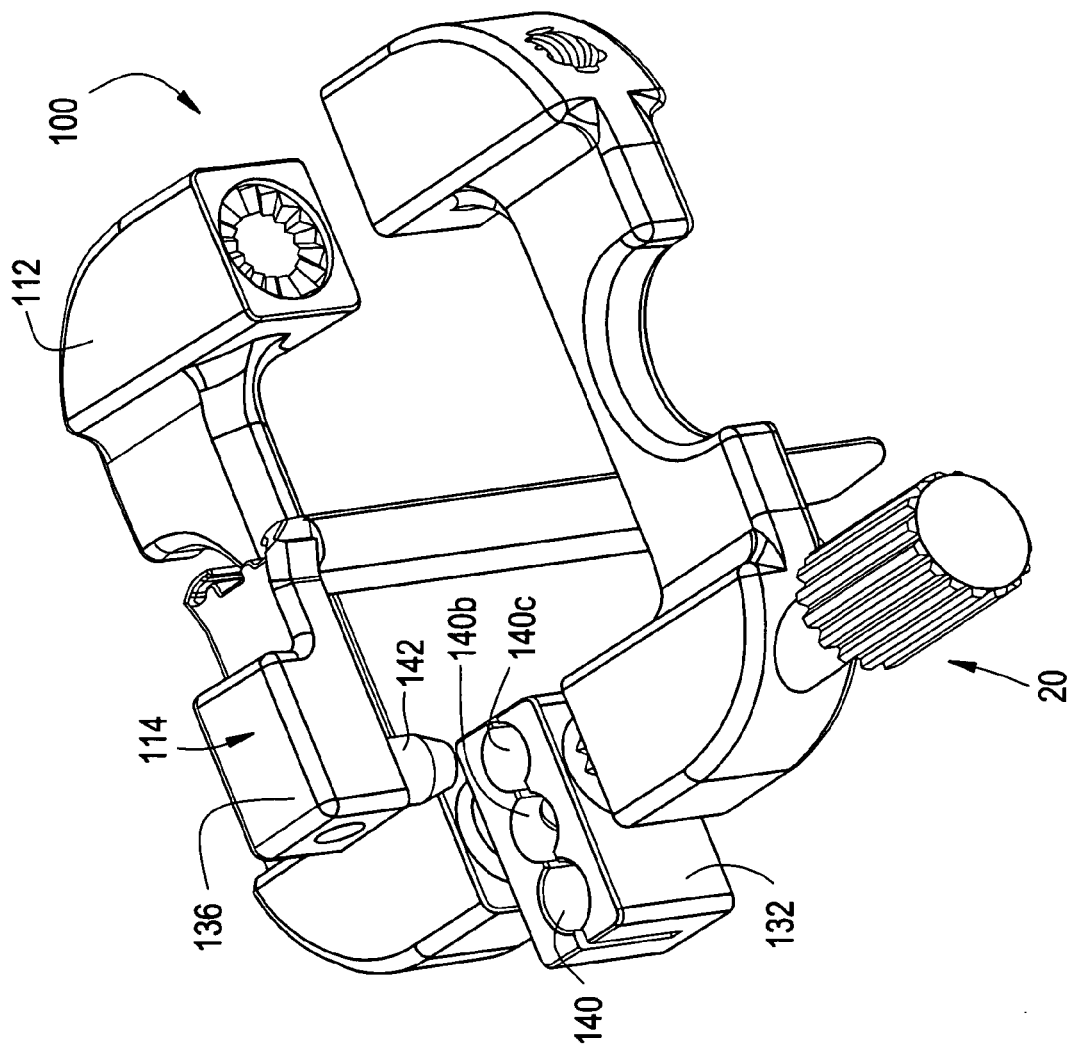

SURGICAL RETRACTOR FOR USE WITH MINIMALLY INVASIVE SPINAL STABILIZATION SYSTEMS AND METHODS OF MINIMALLY INVASIVE SURGERY

BACKGROUND

In surgical procedures, it is important to minimize trauma to the patient and damage to tissue to facilitate patient recovery. One way to accomplish this is to minimize the size of the incision for the surgical procedure and minimize the cutting of tissue to access the target anatomy. A number of retractors are available that are designed to expand a small surgical incision and provide access to a surgical site. Such retractors typically include two or more retractor blades that separate to expand the incision and create an access channel through which to conduct the surgical procedure. One problem with such retractors is that the retractors generally require a bed-mounted arm to maintain the retractor in place during surgery. Such retractor arms are frequently cumbersome to use, are often in the way of the surgeon and operating room staff, and generally are not effective at maintaining the retractor in place.

SUMMARY

Disclosed herein are surgical retractors that may be positioned without the need for a bed-mounted arm or other mechanism connecting the retractor to the bed. The surgical retractors disclosed herein may be anchored to the patient's anatomy by connecting the retractor to anchor extensions connected to bone anchors implanted in the patient. Also disclosed herein are methods of minimally invasive surgery employing a self-retaining surgical retractor.

In accordance with one exemplary embodiment, a surgical retractor for use with a spinal stabilization system including a plurality of bone anchors and a plurality of anchor extensions may comprise a frame positionable between a first anchor extension connected to a first bone anchor implanted in a first vertebra and a second anchor extension connected to a second bone anchor implanted in a second vertebra and a first retractor blade connectable to the frame for retracting tissue between the first anchor extension and the second anchor extension.

In accordance with another exemplary embodiment, a surgical retractor may comprise a frame including a first segment and a second segment, a first retractor blade connectable to the frame, and a second retractor blade connectable to the frame. The first segment of the frame may include an arcuate notch at first end of the frame and the second segment of the frame may include an arcuate notch at second end of the frame opposite the first end of the frame. The first and second retractor blades, when connected to the frame, cooperate to provide an access channel for accessing target anatomy. The first and second segments of the frame cooperate to provide an opening to the access channel.

In accordance with another exemplary embodiment, a method of stabilizing a first vertebra relative to a second vertebra may comprise positioning a first bone anchor in a first vertebra, positioning a second bone anchor in a second vertebra, connecting a first anchor extension to the first bone anchor, and connecting a second anchor extension to the second bone anchor. The first anchor extension extending from the first bone anchor toward the skin and the second anchor extension extending from the second bone anchor toward the skin. The exemplary method may include positioning a retractor between the first anchor extension and the second anchor extension to provide access to spinal anatomy and connecting a stabilizing element to the first bone anchor and the second bone anchor.

BRIEF DESCRIPTION OF THE FIGURES

These and other features and advantages of the surgical retractors and methods disclosed herein will be more fully understood by reference to the following detailed description in conjunction with the attached drawings in which like reference numerals refer to like elements through the different views. The drawings illustrate principles of the surgical retractors and methods disclosed herein and, although not to scale, show relative dimensions.

FIG. 6 is an exploded perspective view of another exemplary embodiment of a surgical retractor;

DETAIL DESCRIPTION OF EXEMPLARY EMBODIMENTS

Figure 1:
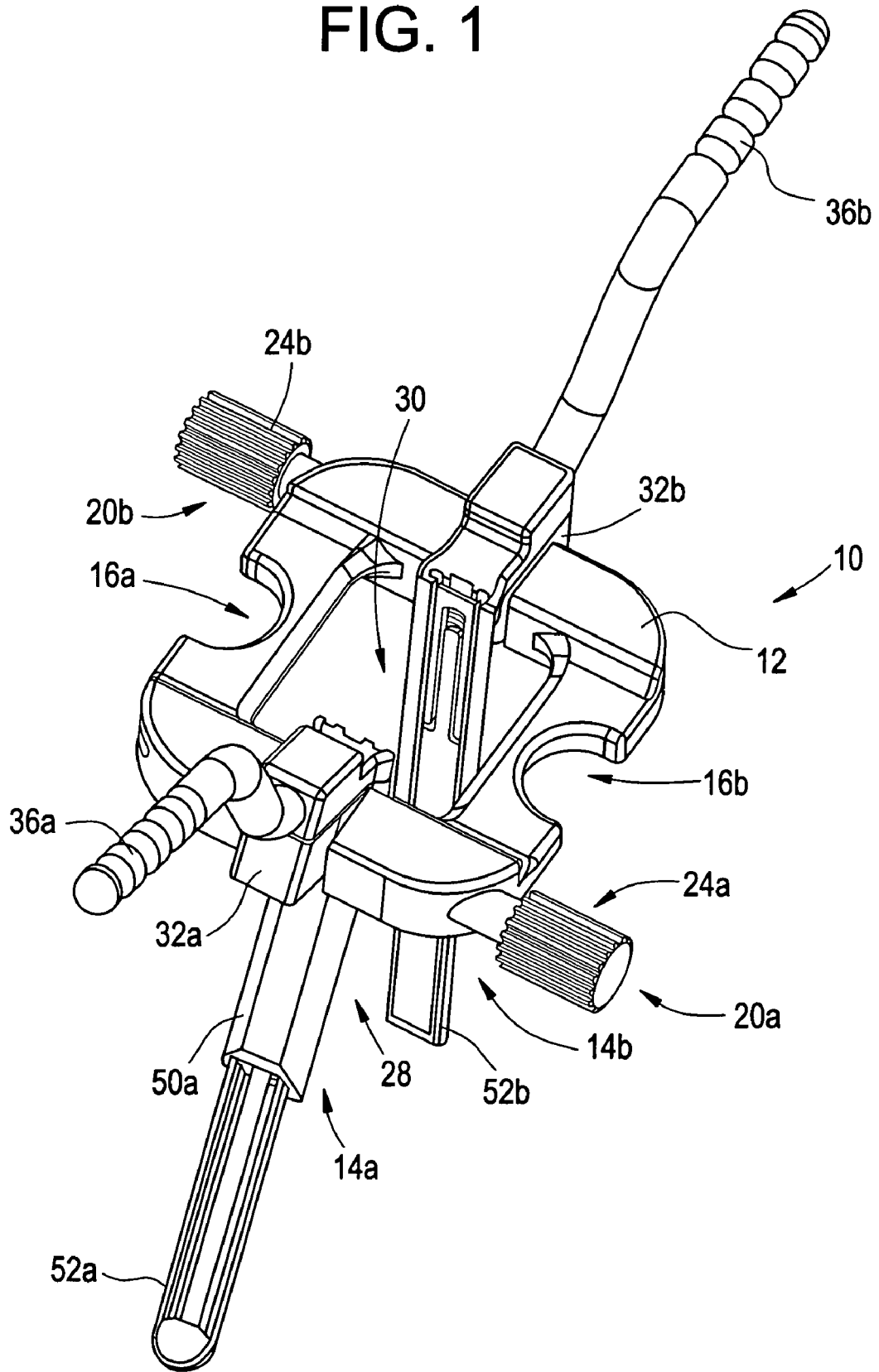
FIG. 1 is a perspective view of an exemplary embodiment of a surgical retractor, illustrating the retractor in an expanded configuration.
Figure 2:
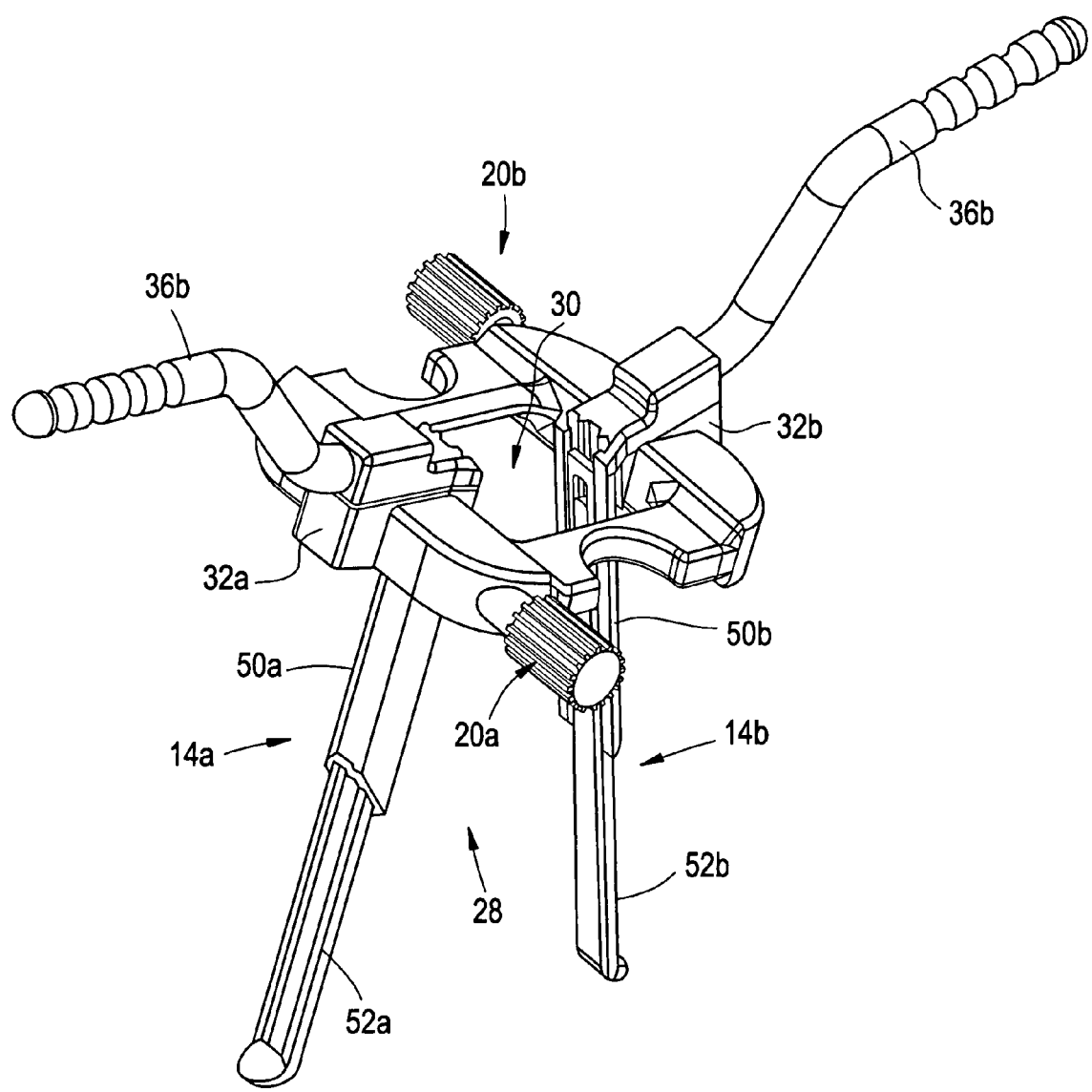
FIG. 2 is a perspective view of the surgical retractor of FIG. 1, illustrating the retractor in an expanded configuration.
Figure 3:
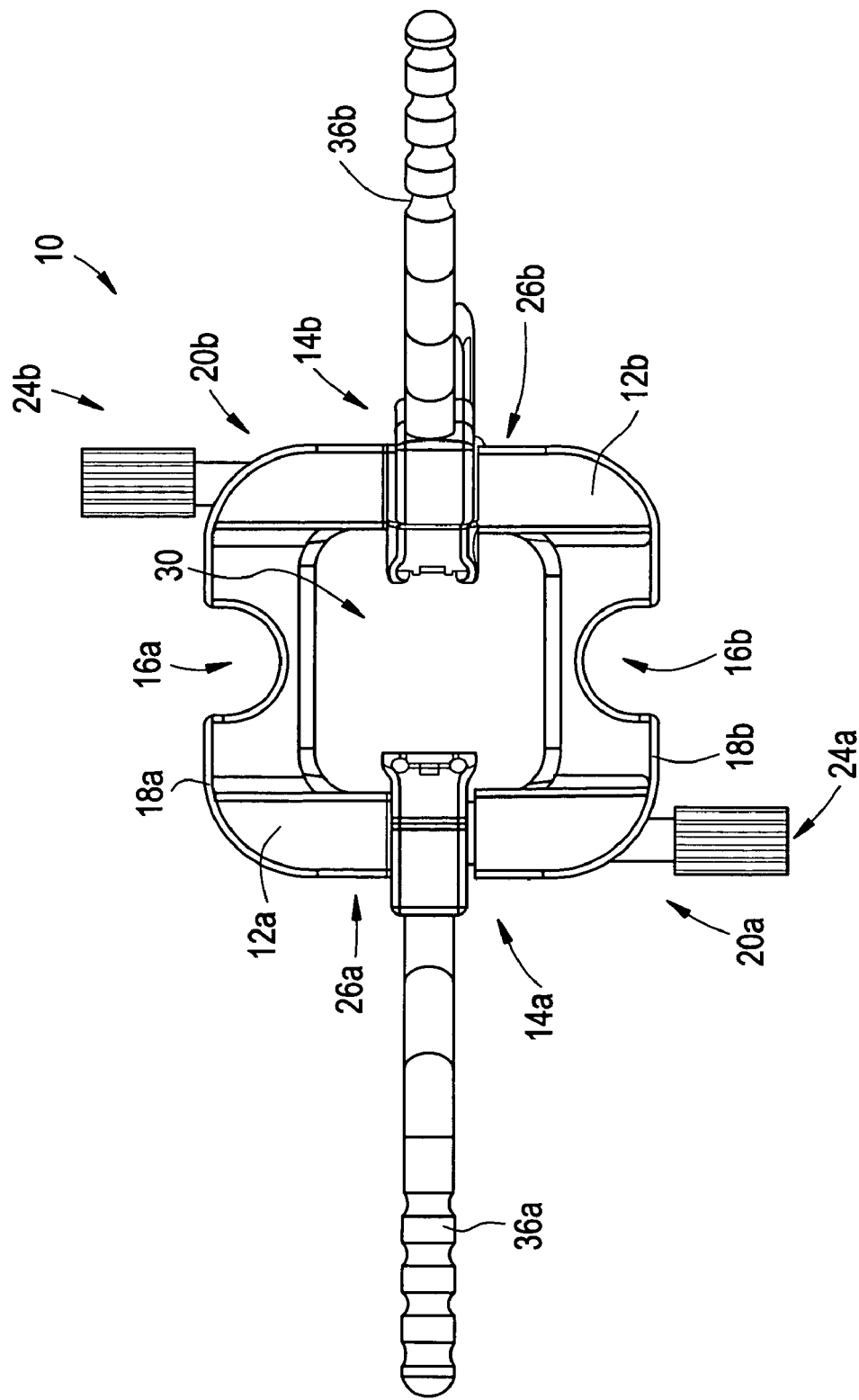
FIG. 3 is a top view of the retractor of FIG. 1.
Figure 4:
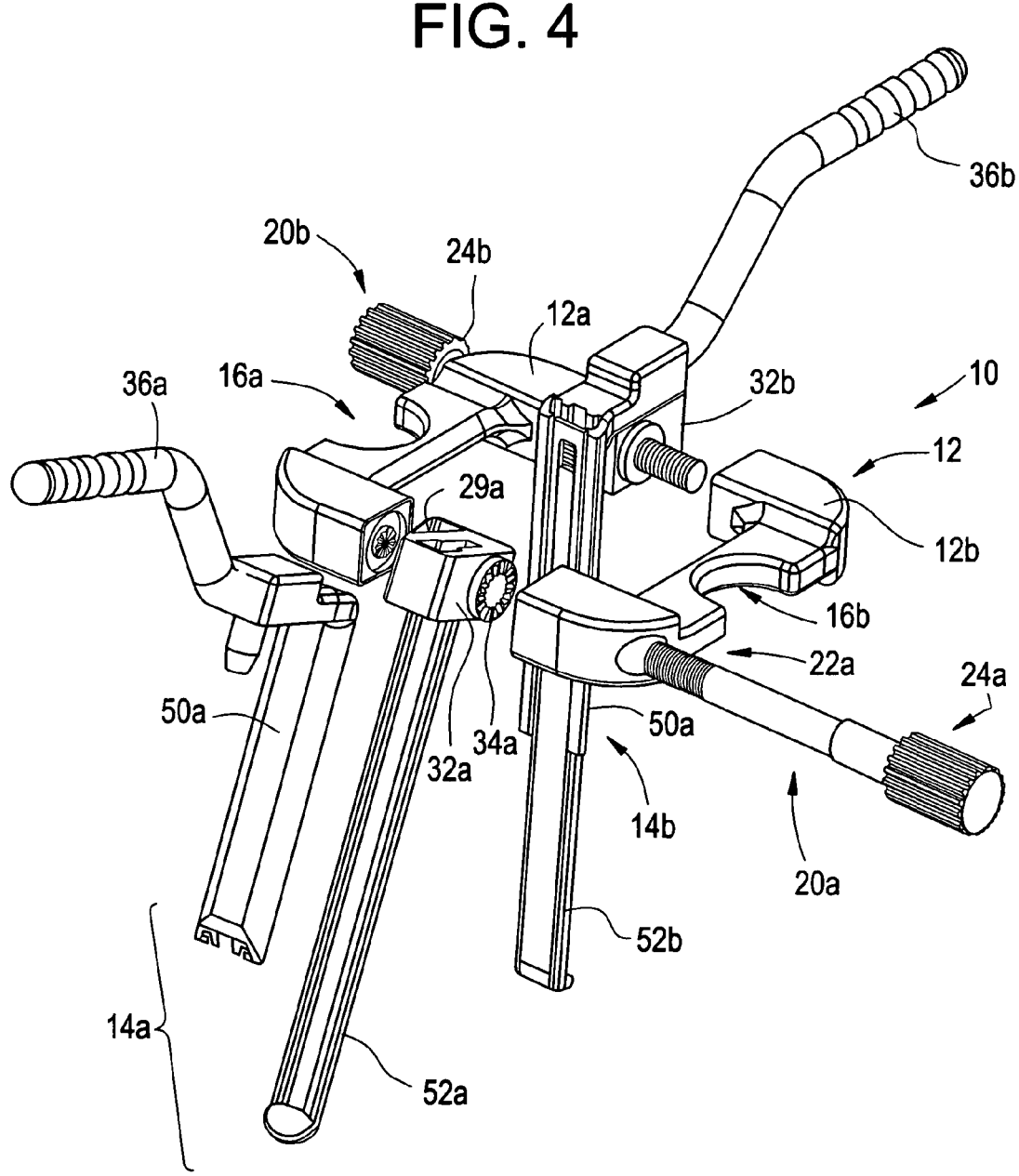
FIG. 4 is an exploded view of the retractor of FIG. 1.

Certain exemplary embodiments will now be described to provide an overall understanding of the principles of the structure, function, manufacture, and use of the surgical retractors and methods disclosed herein. One or more examples of these embodiments are illustrated in the accompanying drawings. Those of ordinary skill in the art will understand that the surgical retractors and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5C illustrate an exemplary embodiment of a surgical retractor 10 suitable for providing a selectively expandable access channel through which a surgical procedure may be performed on target anatomy. The exemplary surgical retractor is particularly suited for minimally invasive spinal surgery and may be used in connection with a spinal stabilization system that is operable to stabilize two or more vertebra. As discussed in more detail below, the surgical retractor 10 may be anchored to the patient's anatomy, for example, one or more vertebrae, by engaging the retractor to the anchor extensions of a spinal stabilization system, thus, eliminating the need to use a bed-mounted arm to maintain the retractor in position relative to the patient.

Referring to FIGS. 1-4, the surgical retractor 10 may include a frame 12 that is engageable to one or more anchor extensions connected to a respective bone anchor that is anchored to the patient's anatomy. For example, the frame 10 may be positionable between a first anchor extension connected to a first bone anchor and a second anchor extension connected to a second bone anchor. In addition, the surgical retractor 10 may include one or more retractor blades 14 connectable to the frame 12 of the retractor 10 for retracting tissue proximate the anchor extension that the frame 12 is engaged to. In the exemplary embodiment, for example, the retractor 10 includes a first retractor blade 14a and a second retractor blade 14b connectable to the frame 12 and positioned on opposite sides of the frame 12. In alternative embodiments, additional retractor blades 14 may be connected to the frame 12 and/or the retractor blades may be positioned on the same side of the frame 12.

Continuing to refer to FIGS. 1-4, the frame 12 of the exemplary retractor 10 may include a first segment 12a for engaging a first anchor extension and a second segment 12b for engaging a second anchor extension. The first segment 12a and the second segment 12b may include one or more features for engaging an anchor extension. In the exemplary embodiment, for example, the first segment 12a may include a first notch 16a at a first end 18a of the first segment 12a. The second segment 12b may include a second notch 16b at a first end 18b of the second segment 12b. The first notch 16a and the second notch 16b may have a size and shape that approximates and is complementary to the size and shape of the anchor extension that the first segment 12a or second segment 12b is to engage. In the case of tubular shaped anchor extensions, for example, the first notch 16a and the second notch 16b may be arcuate in shape having a curvature that approximates and is complimentary to the curvature of the outer diameter of the respective anchor extension.

In certain exemplary embodiments, including the exemplary illustrated embodiment, the first segment 12a and the second segment 12b may be adjustable relative to one another. For example, the exemplary retractor 10 may include a frame adjustment mechanism that facilitates adjustment of the first segment 18a and the second segment 18b relative to one another. The frame adjustment mechanism, in the exemplary retractor 10, includes a pair of threaded shafts 20a and 20b that interconnect the first segment 18a and the second segment 18b and permit motion of the first segment 18a and the second segment 18b along the axes of the shafts 20a,b. The first shaft 20a and the second shaft 20b may be bolt shaped having a threaded first end 22a,b and a second end 24a,b configured as a handle to facilitate rotating of the respective shaft. The first segment 18a may be configured to receive the first end 22a of the first shaft 20a and the second end 24b of the second shaft 20b. In particular, the first segment 12a may include an internally threaded first opening 29a for receiving the threaded first end 22a of the first shaft 20a and the second end 26a of the first segment 12a my include a second non-threaded opening (not illustrated) for receiving the second end 24b of the second shaft 20b. The second segment 12b may be analogously configured to receive the first end 22b of the second shaft 20b and the second end 24a of the first shaft 20a. Rotation of the first shaft 20a and the second shaft 20b in a first direction causes the second end 26a of the first segment 12a and the second end 26b of the second segment 12b to converge and rotation of the of the first shaft 20a and the second shaft 20b in a second direction causes the second end 26a of the first segment 12a and the second end 26b of the second segment 12b to diverge.

In the exemplary embodiment, the retractor blades 14a and 14b extend from the frame 12 and cooperate to provide an access channel 28 for accessing target anatomy through the retractor 10. The first segment 12a and the second segment 12b cooperate to provide an opening 30 to the access channel 28. In the exemplary embodiment, the first segment 12a and the second segment 12b may be approximately U-shaped, providing an opening 30 that is approximately rectilinear in shape. In alternative embodiments, the frame 12 may be configured to provide an opening 30 with different shapes, including, for example, oval and circular.

The retractor blade(s) 14 may be connected to the frame 12 to permit the retractor blade 14 to be adjustable relative to the frame 12 and, thus, to permit expansion of the access channel 28. In certain embodiments, for example, including the illustrated exemplary embodiment, a retractor blade 14 may be rotatably connected to the frame 12 to permit the retractor blade 14 to rotate relative to frame 12. In particular, first blade 14a may be rotatably connected to the one side of the frame 12 and the second blade 14b may rotatably connected to the other side of the frame 12. The first blade 14a and the second blade 14b may be rotatably connected to the first segment 12a and/or the second segment 12b. Alternatively, the frame 12 may include a first intermediate segment 32a interposed between the first segment 12a and the second segment 12b and a second intermediate segment 32b interposed between the first segment 12a and the second segment 12b and positioned opposite the first intermediate segment 32a. The first intermediate segment 32a may be rotatable relative to the frame 12 about a first axis intersecting the first segment 12a and the second segment 12b and the second intermediate segment 32b may be rotatable relative to the frame 12 about a second axis intersecting the first segment 12a and the second segment 12b. In the exemplary embodiment, the first shaft 20a is positioned through an opening in the first intermediate segment 32a and the first shaft 20a defines the first axis about which the first intermediate segment 32a rotates. The second shaft 20b is positioned through an opening in the second intermediate segment 32b and the second shaft 20b defines the second axis about which the second intermediate segment 32b rotates. The first retractor blade 14a may be connected to the first intermediate segment 32a and may rotate with the first intermediate segment 32a relative to the frame 12 and the second retractor blade 14b may be connected to the second intermediate segment 32b and may rotate with the second intermediate segment 32b relative to the frame 12.

The retractor may include a mechanism for selective locking the rotational position of the first intermediate segment 32a and the rotational position of the second intermediate segment 32b. In the exemplary embodiment, for example, the first intermediate segment 32a may include one or more projections 34a having locking teeth for engaging locking teeth of an analogously constructed projection provided on the either the first segment 12a or the second segment 12b, as in the exemplary illustrated embodiment. The second intermediate segment 32b may include one or more projections having for locking teeth for engaging locking teeth of an analogously constructed projection provided on the either the first segment 12a or the second segment 12b. As the first segment 12a and the second segment 12b converge the locking teeth of one or more projections provided on the first intermediate segment 32a and the second intermediate segment 32b engage locking teeth on a respective projection of either the first segment 12*a* and/or the second segment 12*b* to lock the intermediate segments 32*a,b* in a respective rotational orientation.

In other exemplary embodiments, such as the embodiment illustrated in FIG. 6 described below, one or more of the retractor blades 14 may be laterally adjustable relative the frame 12.

One or more of the retractor blades 14 may include a handle 36 at the proximal end of the retractor blade 14 to facilitate connection of the retractor blade 14 to the frame and to facilitate adjustment of the position of the retractor blade 14 relative to the frame 12.

One or more of the blades 14 of the retractor may have an adjustable length, e.g. the blade may telescope to selectively adjust the length of the blade. Referring to the exemplary embodiment illustration in FIGS. 1-4, for example, one or more of the blades 14 may include a primary blade 50 and an adjustable blade 52 that is operatively coupled to the primary blade 50 and is adjustable relative to the primary blade 50 along the length of the primary blade 50. In the exemplary embodiment, blades 14*a,b* are adjustable in length and include a respective primary blade 50*a,b* and a respective adjustable blade 52*a,b*. Exemplary tissue engaging blades having an adjustable length are disclosed in U.S. Patent Application Publication No. 2005-0137461 A1, which is incorporated herein by reference. The telescoping blades may include a mechanism for selectively adjusting the position of the adjustable blade 52 relative to the primary blade 50. For example, the primary blade 50 may include a plurality of teeth extending along the longitudinal axis of the primary blade 50 and the adjustable blade 52 may include a flexible tab for engaging the teeth of the primary blade 50. The blades 14 may be inserted through an incision with the adjustable blades 52 in place, as in the case of the exemplary retractor 10 illustrated in FIGS. 1-4. Alternatively, the blades 14 may be inserted through an incision without the adjustable blades in place. In such embodiments, the primary blades 50 may be inserted and one or more adjustable blades may be added after insertion.

The components of the retractors disclosed herein may be manufactured from any biocompatible material including metals, such as stainless steel or titanium, polymers, or composite materials. The components, such as the blades and the frame, may be constructed from the same or different materials.

Figure 5A:
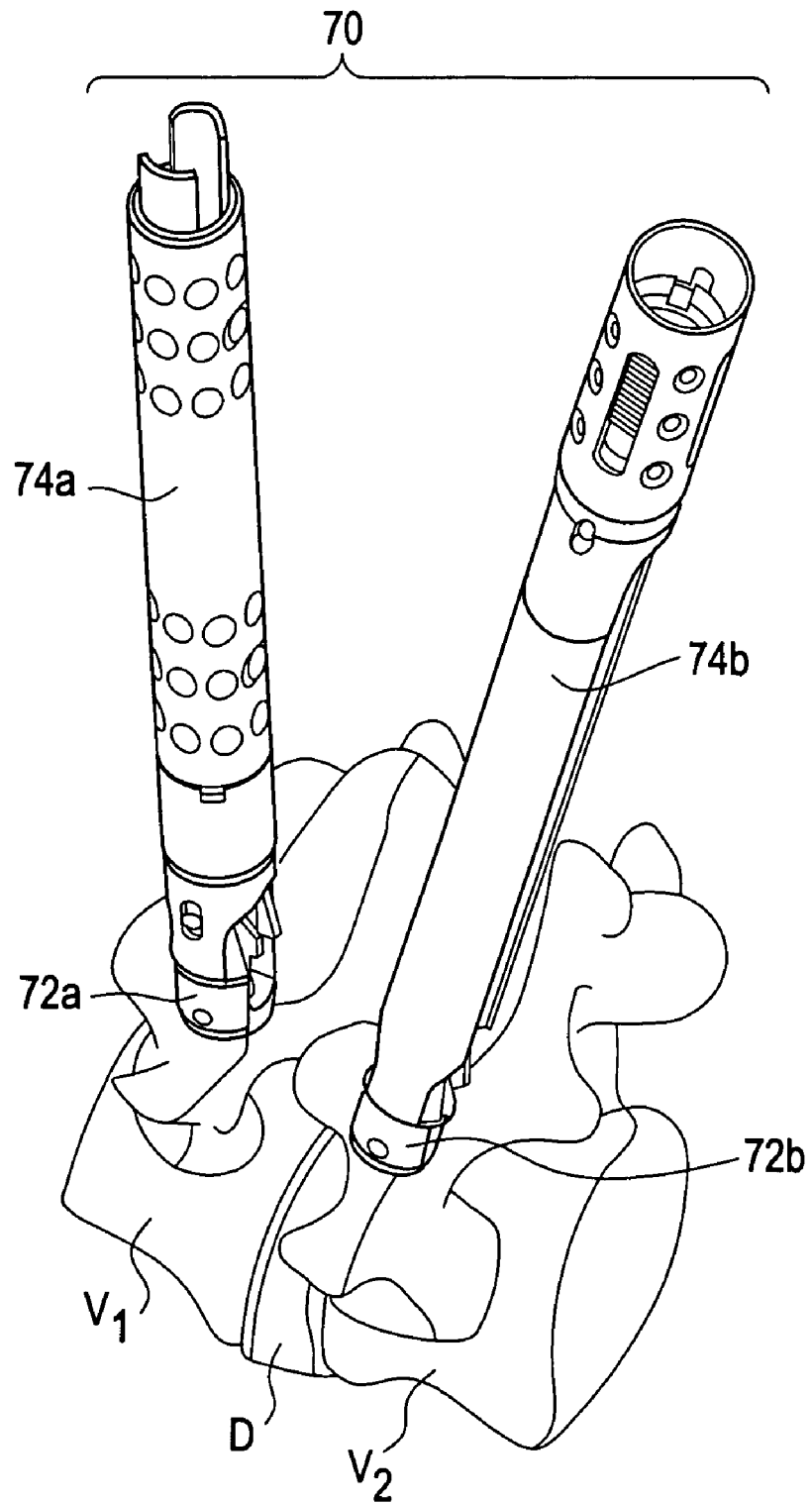
FIGS. 5A-5C are perspective views of the retractor of FIG. 1, illustrating an exemplary method of stabilizing two vertebrae.
Figure 5B:
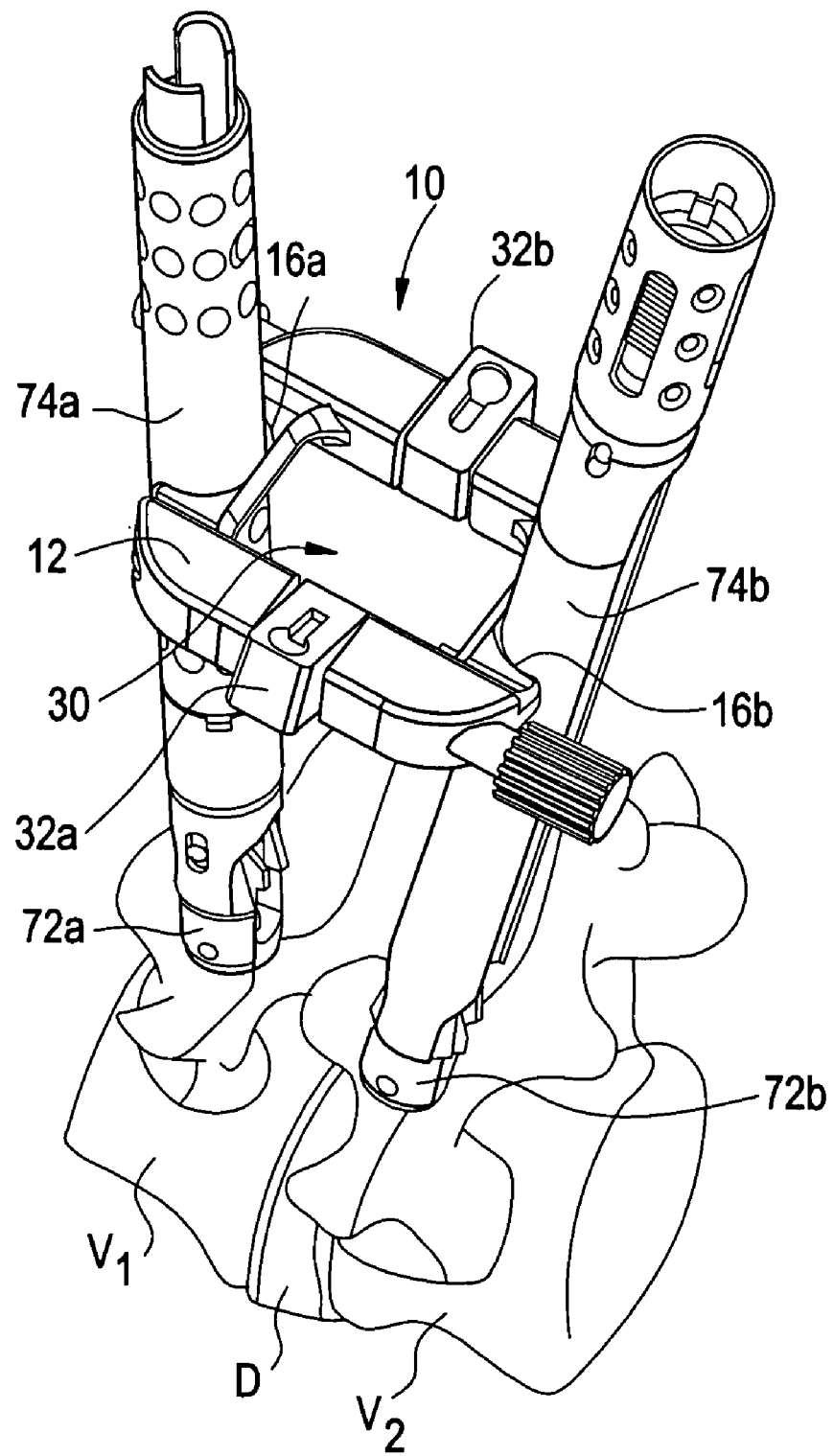
Figure 5C:
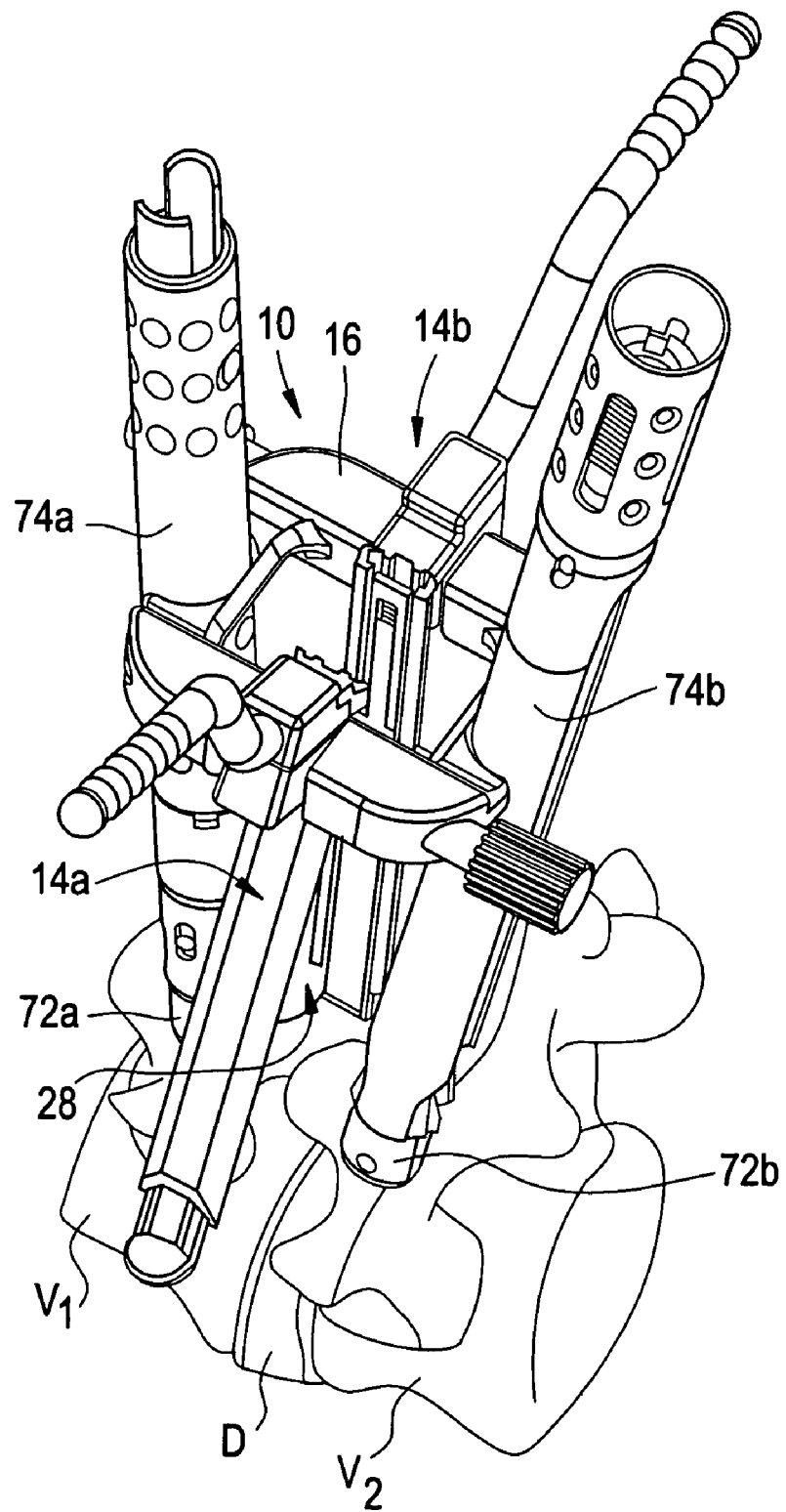

An exemplary method of providing access to spinal anatomy employing exemplary retractor 10 is illustrated in FIGS. 5A-C. In the exemplary method, the retractor 10 is used in conjunction with a spinal stabilization system, in particular a minimally invasive spinal stabilization system 70 for stabilizing one or more vertebra relative to another vertebra. The exemplary minimally invasive spinal stabilization system 70 may include a plurality of bone anchors 72, such as, for example, polyaxial pedicle screws, a plurality of anchor extensions 74, and a plurality of spinal stabilization elements that may connect two or more bone anchors 72 to stabilize vertebrae. The spinal stabilization elements may be, for example, a rigid spinal rod constructed of a metal, e.g., stainless steel or titanium, or other material or a dynamic spinal connection element that permits motion between the connected bone anchors. An exemplary minimally invasive spinal stabilization system is the VIPER Percutaneous Fixation System available from DePuy Spine, Inc. of Raynham, Mass. Exemplary spinal stabilization systems are disclosed in U.S. Patent Application Publication No. 2005-0131422 and U.S. Patent Application Publication No. 2005-0131408, both of which are incorporated herein by reference.

Referring to FIG. 5A, a first bone anchor 72*a* may be positioned in a first vertebra V1 and a second bone anchor 72*b* may be positioned in a second vertebra V2, which is adjacent the first vertebra V2. The first bone anchor 72*a* and the second bone anchor 72*b* may be positioned through separate percutaneous incisions or through a single incision. The first anchor extension 74*a* may be connected to the first bone anchor 72*a* and a second anchor extension 74*b* may be connected to the second bone anchor 72*b*. The first anchor extension 74*a* and the second anchor extension 74*b* extend from the respective bone anchor 72*a,b* toward the skin. In the exemplary embodiment, for example, the first anchor extension 74*a* and the second anchor extension 74*b* extend from the respective bone anchor 72*a,b* through the skin incision. The exemplary anchor extensions 74*a,b* are generally tubular in-shape having a central lumen through which instruments and implants, including the closure mechanism for the respective bone anchor and/or a spinal stabilization element, may be delivered to the respective bone anchor. The bone anchors 72*a*,72*b* may be positioned in a respective vertebra with a respective anchor extension connected thereto or, in alternative embodiments, the anchor extensions may be connected after the bone anchors are positioned in the vertebrae.

Referring to FIG. 5B, a retractor, such as exemplary retractor 10, may be positioned between the first anchor extension 74*a* and the second anchor extension 74*b* to provide access to the first vertebra, the second vertebra, the disk D between the vertebra, or other anatomy proximate the first vertebrae V1 and the second vertebrae V2. In the exemplary embodiment, the first notch 16*a* receives the first anchor extension 74*a* and the second notch 16*b* receives the second anchor extension 74*b* to engage the frame 12 to the first anchor extension 74*a* and the second anchor extension 74*b*. The retractor 10 may be anchored to the patient by engagement of the frame 12 to the bone anchor extensions 74*a,b*.

One or more retractor blades 14 may be added to the frame 12 to retract tissue between the anchor extensions 74*a,b*. In the exemplary embodiment, first retractor blade 14*a* may be connected to first intermediate segment 32*a* and a second retractor blade 14*b* may be connected to the second intermediate segment 32*b*, as illustrated in FIG. 5C. The rotational position of the first blade 14*a* and/or the rotational position of the second blade 14*b* may be adjusted to selectively expand the access channel 28. The rotational position of the first blade 14*a* and/or the second blade 14*b* may be fixed by converging the first segment 12*a* and the second segment 12*b* into contact. In addition, the length of the first blade 14*a* and/or the second blade 14*b* may be adjusted by adjusting the adjustable blade relative to the primary blade, thereby increasing the length of the access channel.

Any number of surgical procedures may be performed through the access channel 28 of the retractor 10. Exemplary surgical procedures may include, for example, placement of the spinal stabilization element, removing of disc material from the disk D, insertion of bone fusion promoting material, removal of portions of the vertebrae, and insertion of other spinal implants, including an artificial disk.

The spinal stabilization element may be inserted through the retractor 10, through one or both of the anchor extensions 74*a,b* or through the retractor 10 and one or both of the anchor extensions. For example, the stabilizing element may be positioned through the first anchor extension and may be rotated, beneath the skin or beneath the facia, toward the second bone anchor to connect to the second bone anchor. Alternatively, a first end of the stabilizing element may be positioned in the first anchor extension and a second end of the stabilizing element may be positioned in the second anchor extension and the stabilization element may be moved toward the first bone anchor and the second bone anchor. Alternatively, the stabilizing element may be inserted independent of the anchor extensions through the incision or through the retractor.

After completion of the desired surgical procedures, the retractor 10 and anchor extensions may be removed from the incision.

Although the exemplary procedure involves two adjacent vertebrae, one skilled in the art will appreciate that that exemplary retractor may be used with three or more vertebrae and with non-adjacent vertebrae.

FIG. 6 illustrates an alternative embodiment of a retractor 100 similar in construction to the exemplary retractor 10 described above. The exemplary retractor 100 permits lateral and rotational adjustment of one or more retractor blades 114. In the exemplary embodiment, the retractor 100 includes at least one intermediate segment 132 have a plurality of openings 140 for selective placement of the retractor blade 114. In the exemplary embodiment, three openings 140a-c are provided any number of openings, e.g., two or more, may be provided to provide alternative lateral positions for the retractor blade 114. The proximal end 136 of the blade 114 may include a post 142 complimentary in size and shape to the openings 140a-c. The openings 140a-c are arranged to provide alternative lateral positions for the retractor blade 114. Intermediate segment 132 may rotate relative to the frame 112 to permit rotational adjustment of the blade 114 and, in this regard, may be constructed analogously to the first intermediate segment 32a and the second intermediate segment 32b described above.

Figure 7:
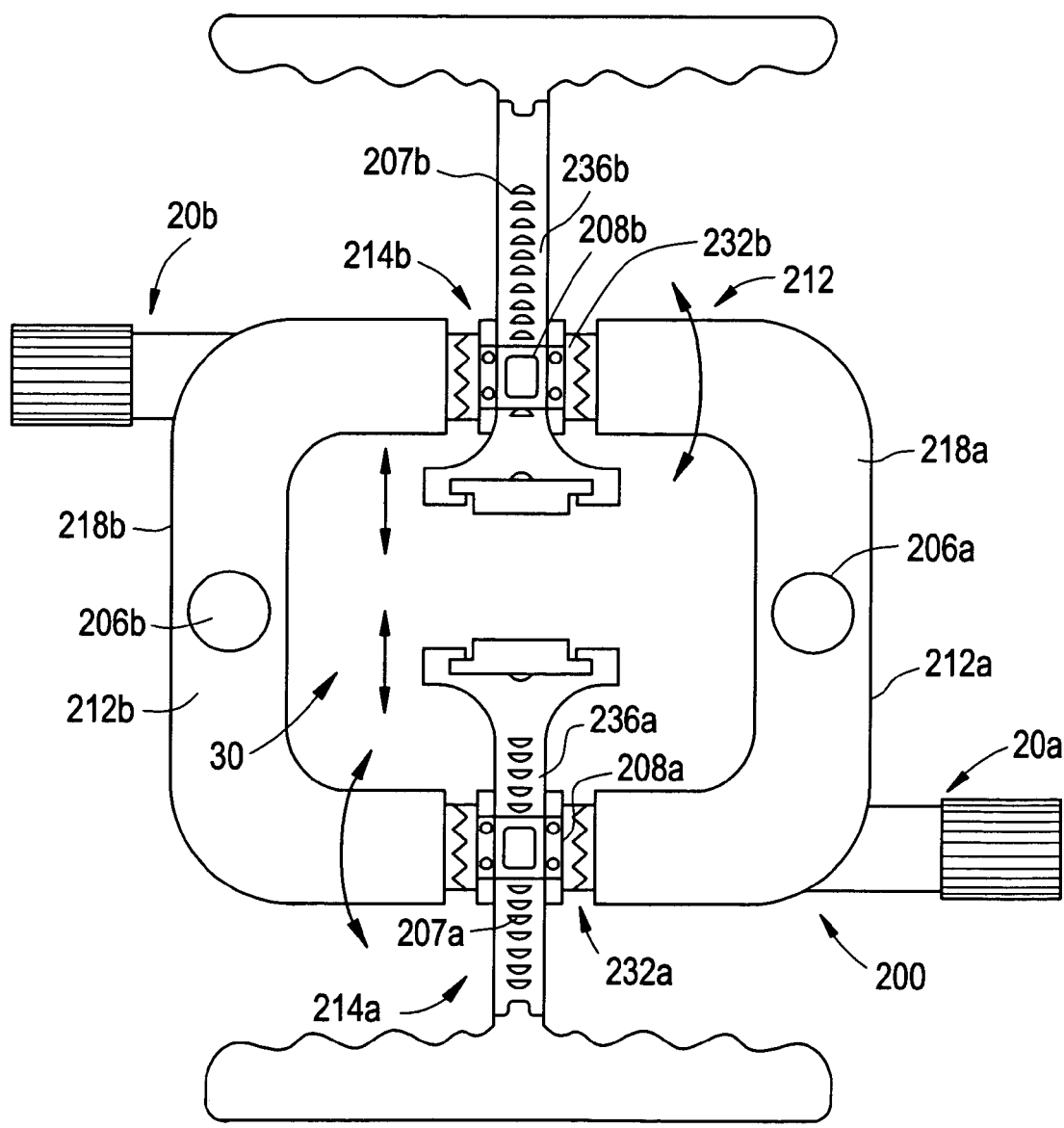
FIG. 7 is a top view of another exemplary embodiment of a surgical retractor.

An alternative embodiment of a retractor 200 is illustrated in FIG. 7. The exemplary retractor 200 includes a first segment 212a and the second segment 212b that may include one or more features for engaging an anchor extension. In the exemplary embodiment, for example, the first segment 212a may include a first opening 206a at a first end 218a of the first segment 212a. The second segment 212b may include a second opening 206b at a first end 218b of the second segment 212b. The first opening 206a and the second opening 206b may have a size and shape that approximates and is complementary to the size and shape of the anchor extension that the first segment 212a or second segment 212b is to engage. In the case of tubular shaped anchor extensions, for example, the first opening 206a and the second opening 206b may be approximately circular in shape having a diameter that approximates and is complimentary to the outer diameter of the respective anchor extension.

Continuing to refer to FIG. 7, the retractor 200 may include one or more retractor blades 214. In the exemplary embodiment, the retractor 200 includes a first retractor blade 214a and a second retractor blade 214b positioned opposite the first retractor blade 214a. The retractor blades 214a,b may be rotationally and laterally adjustable relative to the frame 212 of the retractor 210. For example, the retractor blades 214a,b may be connected to a respective intermediate segment 232a,b of the frame 212 that is rotatably connected to the first segment 212a and the second segment 212b of the frame 212. The intermediate segments 232a,b may be constructed in a manner analogous to the intermediate segments 32a,d, of the exemplary retractor 10 described above. In this configuration, the first retractor blade 214a and the second retractor blade 214b may be rotationally adjusted relative to the frame 212. The retractor blades 214a,b may be laterally adjustable relative to the intermediate segments 232a,b, respectively. For example, the proximal end 236a of the first blade 214a may be positionable through a housing 208a provided on the top surface of the first intermediate segment 232a. The first blade 214a may be laterally adjusted relative to the housing 208a by moving the first blade 214a along the axis of the proximal end 236a of the first blade 214a. In the exemplary embodiment, the proximal end 236a of the first blade 214a may be oriented approximately perpendicular to the tissue engaging distal end of the first blade 214a. The proximal end 236b of the second blade 214b may be positionable through a housing 208b provided on the top surface of the second intermediate segment 232b. The second blade 214b may be laterally adjusted relative to the housing 208b by moving the second blade 214b along the axis of the proximal end 236b of the second blade 214b. In the exemplary embodiment, the proximal end 236b of the second blade 214b may be oriented approximately perpendicular to the tissue engaging distal end of the second blade 214b. A ratchet mechanism or other mechanism may be provided to selectively fix the lateral position of one or more of the retractor blades 214. For example, the proximal ends 236a,b of the first blade 214a and the second blade 214b may include a plurality of teeth 207a,b that may be selectively engaged by a tooth, pawl, gear, or other mechanism provided on the housing 208a,b.

Figure 8:
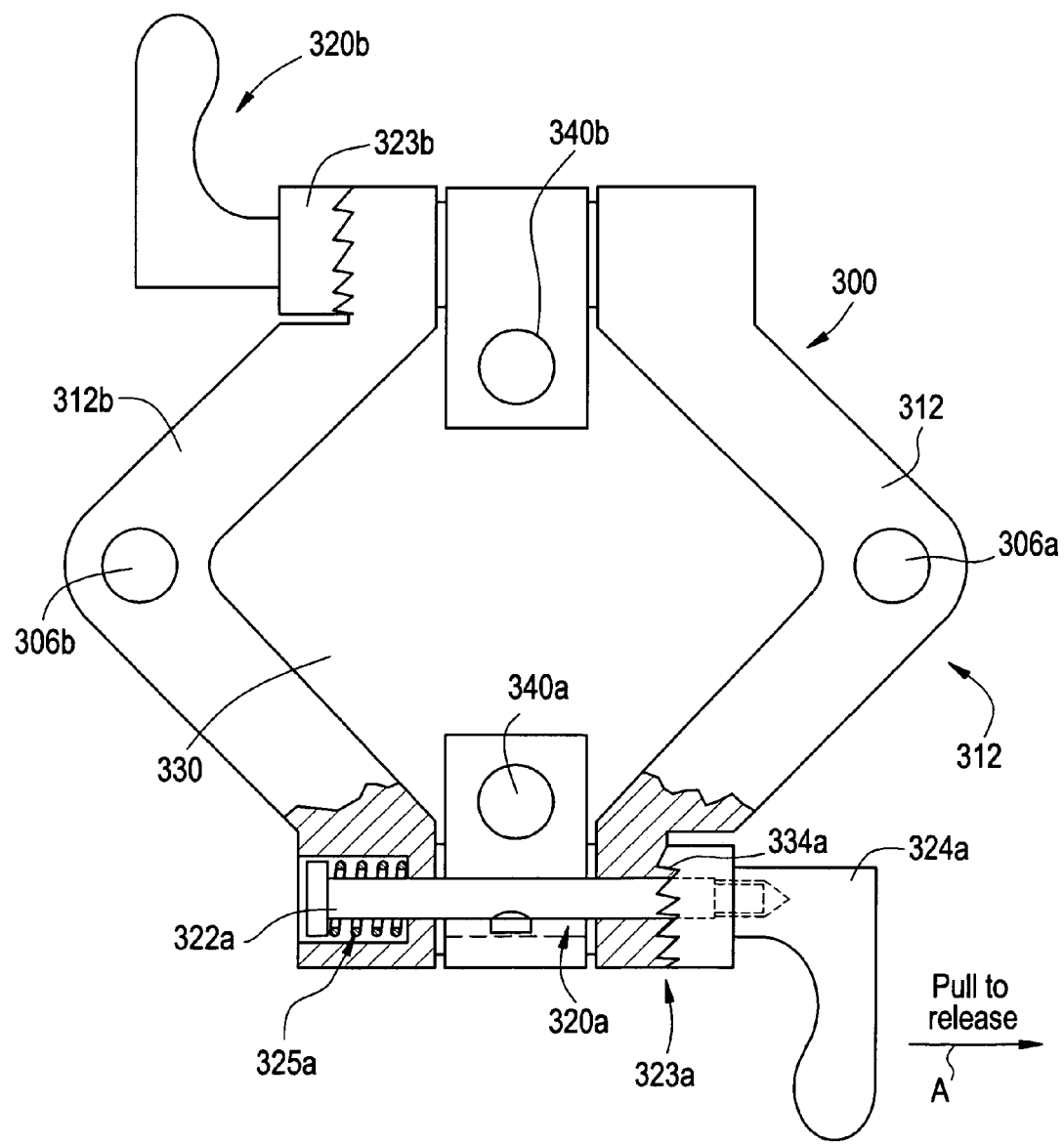
FIG. 8 is a top view of another exemplary embodiment of a surgical retractor.

FIG. 8 illustrates another exemplary embodiment of a retractor 300. The exemplary retractor 300 includes a frame 312 comprising a first segment 312a and a second segment 312b that cooperate to provide an opening 330 to the access channel provided by the retractor 300. The first segment 312a and the second segment 312b are approximately V-shaped to provide an access opening 330 having an approximately diamond shape. The first segment 312a and the second segment 312b may include a first opening 306a and a second opening 306b, respectively, for engaging a respective anchor extension. The frame 312 of the exemplary retractor 300 may include a first intermediate segment 332a and a second intermediate segment 332b that may be constructed analogously to the intermediate segments 32a,b of the exemplary retractor 10 described above. The first intermediate segment 332a and the second intermediate segment 332b each may include one or more openings 340a,b to facilitate connection of a retractor blade to the intermediate section. The first intermediate segment 332a and the second intermediate segment 332b may be rotatably connected to the first segment 312a and the second segment 312b of the frame 312. In the exemplary embodiment, for example, a first shaft 320a may be positioned through the first segment 312a, the intermediate segment 332a, and the second segment 312b and the first intermediate segment 332a may be rotatably adjustable relative to the first shaft 320a. The distal end 322a of the first shaft 320a is received in an opening provided in the second segment 312b. The proximal end 324a of the first shaft 320a may include a handle to facilitate adjustment of the first shaft 320a. An annular member 323b having a locking teeth 334a for engaging locking teeth provided on the first segment 312a of the frame 312. Displacing the first shaft 312a in a first direction, away from the frame 312, indicated by arrow A, allows the first segment 312a and the second segment 312b to be displaced from one another and allows the first intermediate segment 332a to rotate relative to one another. Movement of the first shaft 312a in a second direction, opposite the first direction, causes the first segment 312a and the second segment 312b to converge and, upon engagement of the locking teeth 334a with the locking teeth provided on the frame 312, inhibits rotation of the first intermediate member 332a. A spring 325a may be provided to bias the first segment 312a and the second segment 312b into contact. The retractor 300 may include a second shaft 320b that is constructed and operable in a manner analogous to the first shaft 320a.

While the surgical retractors and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A method of accessing anatomy proximate to a first vertebra and a second vertebra, the method comprising:
   positioning a first bone anchor in a first vertebra;
   positioning a second bone anchor in a second vertebra;
   connecting a first anchor extension to the first bone anchor, the first anchor extension extending from the first bone anchor toward the skin;
   connecting a second anchor extension to the second bone anchor, the second anchor extension extending from the second bone anchor toward the skin
   positioning a retractor between the first anchor extension and the second anchor extension to provide access to spinal anatomy proximate to the first vertebra and the second vertebra, the retractor having a frame including a first segment and a second segment, the first segment including an arcuate notch at a first end of the frame, the second segment including an arcuate notch at a second end of the frame opposite the first end of the frame, the frame further including a first intermediate segment interposed between the first segment and the second segment and a second intermediate segment interposed between the first segment and the second segment, the first intermediate segment positioned opposite the second intermediate segment, positioning the retractor comprising,
      positioning the first anchor extension in the first arcuate notch,
      positioning the second anchor extension in the second arcuate notch, the first segment and the second segment of the frame being positioned between the first anchor extension and the second anchor extension,
      connecting a first retractor blade to the first intermediate segment, and
      connecting a second retractor blade to the second intermediate segment, positioning the first end of a stabilizing element in the first anchor extension,
   rotating the first end of the stabilizing element from the first anchor extension beneath the skin to at least one of the second anchor extension and the second bone anchor, and
   connecting the stabilizing element to the first bone anchor and the second bone anchor.

2. The method of claim 1, wherein the first vertebra is adjacent the second vertebra.

3. The method of claim 2, further comprising removing disc material from the disk between the first vertebra and the second vertebra through the retractor.

4. The method of claim 3, further comprising inserting bone fusion promoting material between the first vertebra and the second vertebra through the retractor.

5. The method of claim 1, further comprising adjusting the rotational position of the first retractor blade.

6. The method of claim 1, further comprising adjusting the lateral position of the first retractor blade.

7. The method of claim 1, wherein the first anchor is positioned in the first vertebra after the first anchor extension is connected to the first bone anchor and the second anchor is positioned in the second vertebra after the second anchor extension is connected to the second bone anchor.

8. The method of claim 1, wherein the first anchor is positioned in the first vertebra before the first anchor extension is connected to the first bone anchor and the second anchor is positioned in the second vertebra before the second anchor extension is connected to the second bone anchor.

9. The method of claim 1, wherein the first anchor and the second anchor are inserted through a common incision.

10. The method of claim 1, wherein the first anchor and the second anchor are inserted through separate incisions.

* * * * *